United States Patent [19]

Giraldi et al.

[11] 4,118,504
[45] Oct. 3, 1978

[54] ISOINDOLINE DERIVATIVES FOR TREATING PAIN

[75] Inventors: PierNicola Giraldi, Milan; Giuliano Nannini, Bresso (Milan); Willy Logemann, Milan; Raffaele Tommasini, Milan; Ada Buttinoni, Milan; Giovanni Biasoli, Gavirate (Varese), all of Italy

[73] Assignee: Carlo Erba, Milan, Italy

[21] Appl. No.: 763,522

[22] Filed: Jan. 28, 1977

Related U.S. Application Data

[62] Division of Ser. No. 535,793, Dec. 23, 1974, which is a division of Ser. No. 432,490, Jan. 11, 1974, abandoned, which is a division of Ser. No. 194,500, Nov. 1, 1971, abandoned.

[30] Foreign Application Priority Data

Nov. 5, 1970 [IT] Italy .................. 31334 A/70
Nov. 10, 1970 [IT] Italy .................. 31514 A/70

[51] Int. Cl.² ............................................. A61K 31/40
[52] U.S. Cl. ............................................. 424/274
[58] Field of Search ....................................... 424/274

[56] References Cited

U.S. PATENT DOCUMENTS 3,767,805  10/1973  Carney ....................... 424/274

Primary Examiner—Stanley J. Friedman
Attorney, Agent, or Firm—Cameron, Kerkam, Sutton, Stowell & Stowell

[57] ABSTRACT

Isoindoline derivatives are disclosed, as for instance of the formula:

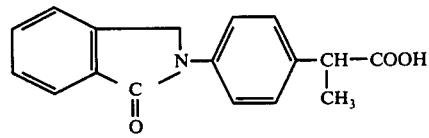

and methods of preparation of these compounds, such as the reaction of o-cyano-benzylbromide with a compound of formula

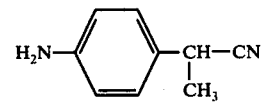

and subsequent saponification.

The compounds possess analgesic and anti-inflammatory activity.

2 Claims, No Drawings

ISOINDOLINE DERIVATIVES FOR TREATING PAIN

This is a Division of application Ser. No. 535,793, filed Dec. 23, 1974, which is a division of Ser. No. 432,490 filed 01-11-74, now abandoned, which is a division of Ser. No. 194,500, filed Nov. 1, 1971, now abandoned.

BACKGROUND OF THE INVENTION

In recent years the search for substances with analgesic and anti-inflammatory activity shifted from the fields of cortisone congeners (still endowed with hormonal actions) and morphine narcotics to other classes of chemical compounds.

While products with undeniable pharmacological activity have been obtained, the problem is far from completely solved, because many of these products are quite toxic and poorly tolerated, causing as they do, among other things, ulcerations, gastrointestinal disturbances, nausea, etc.; furthermore, they cause harmful secondary effects.

Certain isoindoline derivatives have now been found to be characterized by a negligible toxicity and to be tolerated very well, since they cause no secondary effects.

DESCRIPTION OF THE INVENTION

The present invention refers to certain compounds having analgesic and anti-inflammatory activity and to a process for their preparation. The compounds, object of this invention, have the following general formula:

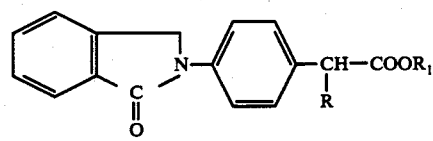
(I)

wherein R is a member selected from the group consisting of hydrogen and lower alkyl of 1 to 4 carbon atoms, and $R_1$ is a member selected from the group consisting of hydrogen, lower alkyl of 1 to 4 carbon atoms and a group of general formula

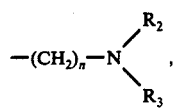

wherein $n$ is 1 or 2 and $R_2$ and $R_3$ are independently selected from the group consisting of hydrogen and lower alkyl of 1 to 4 carbon atoms.

The scope of the invention also comprises the salts of the compounds of general formula (I), wherein $R_1$ is hydrogen, with physiologically acceptable organic or inorganic bases, in particular the salts with N,N-dimethylaminoethanol, as well as the salts of the compounds of general formula (I), wherein $R_1$ is the group

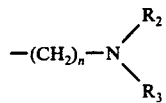

with physiologically acceptable organic or inorganic acids. The compounds of general formula (I) may be prepared by the following methods:

(a) reacting o-cyano-benzylbromide

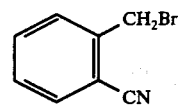

as prepared by bromination of commercially available orthocyano-toluene with $Br_2$ at a temperature of about 150° C., with a compound of general formula

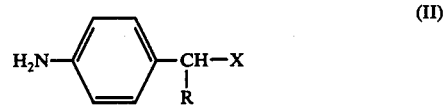
(II)

wherein X is a carbethoxy or a cyano group and R is as defined above, as prepared by reduction with Fe and $NH_4Cl$ or by catalytic hydrogenation of the corresponding nitroderivative, obtained in its turn by nitration of the compound of formula

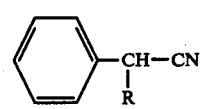

(Bull. Soc. Chim. France, page 866, 1960) with methods described in literature for analogous compounds, at a temperature of about 75° to about 85° C., in polar solvents, such as ethanol, methanol or the like, to form a compound of general formula

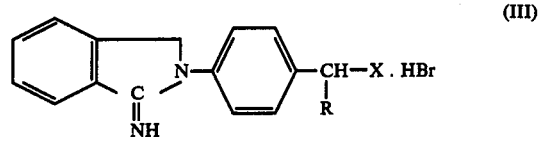
(III)

wherein R and X are as defined above, which is subsequently reacted by saponification with suitable bases, such as, for example, $K_2CO_3$, KOH, or the like, or with suitable acids, such as, for example, conc. $H_2SO_4$, at a temperature of about 75° to about 180° C., to give compounds of general formula (I), wherein $R_1$ is hydrogen, and subsequently, if desired, esterifying at a temperature of about 60° to about 120° C., the compounds of general formula (I), wherein $R_1$ is hydrogen, thus obtained, with the proper alcohols or amino alcohols, according to the usual methods of organic chemistry; or (b) reacting commercially available phthalide

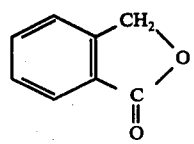

with a compound of general formula (II) at a temperature of about 150° to about 300° C., so obtaining a compound of formula

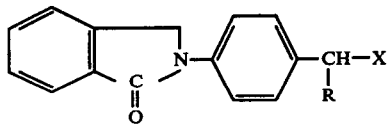 (IV)

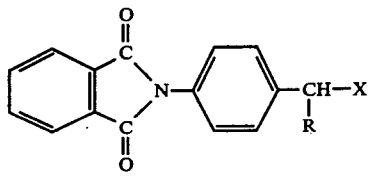 (V)

wherein X and R are as defined above, which is subsequently reacted by saponification with suitable bases, such as, for example, K₂CO₃, KOH, or the like, or with suitable acids, such as, for example, conc. H₂SO₄, at a temperature of about 75° to about 180° C., to give compounds of general formula (I), wherein R₁ is hydrogen, and subsequently, if desired, esterifying at a temperature of about 60° to about 120° C., the compounds of general formula (I), wherein R₁ is hydrogen, thus obtained, with the proper alcohols or amino alcohols according to the usual methods of organic chemistry; or reacting tiophthalide

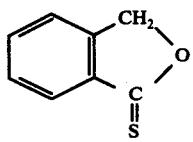

as prepared according to the method of V. Prey and P. Kondler, Monat. für Chemie, 89, 505 (1958), the disclosure of which is hereby incorporated by reference, with a compound of formula (II), at a temperature of about 150° to about 280° C., preferably in sealed tube, so obtaining a compound of formula (IV) which is subsequently reacted by saponification to give compounds of general formula (I), wherein R₁ is hydrogen, which, if desired, are esterified as described in process (a); or (d) reacting commercially available phthalic aldehyde

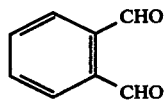

with a compound of formula (II) at a temperature of about 50° to about 150° C. in polar solvents, such as, for example, dimethylformamide, dimethyl sulphoxide, and the like, so obtaining a compound of formula (IV), which is subsequently reacted by saponification to give compounds of general formula (I), wherein R₁ is hydrogen, which, if desired, are esterified as described in process (a); or reacting commercially available phthalic anhydride

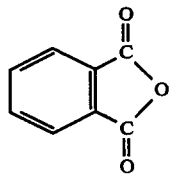

with a compound of formula (II), at a temperature of about 60° to about 150° C., so obtaining a compound of formula wherein X and R are as defined above, which is subsequently reduced with a suitable reducing agent, such as, for example, Zn and CH₃COOH, and the like, at a temperature of about 60° to about 150° C., to give a compound of formula (IV), which is subsequently reacted by saponification to give compounds of general formula (I), wherein R₁ is hydrogen, which, if desired, are esterified as described in process (a); or reacting commercially available compounds of general formula

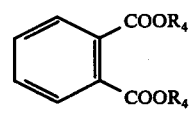 (VI)

wherein the R₄ groups are both hydrogen, both methyl groups, or both ethyl groups, with a compound of formula (II), at a temperature of about 80° to about 280° C., in the presence or absence of a solvent, so obtaining a compound of formula (V), wherein X and R are as defined above, which is subsequently reduced to give a compound of formula (IV), which is then saponified to give compounds of general formula (I), wherein R₁ is hydrogen, which, if desired, are esterified as described in process (a), From the above reaction sequences it appears evident that if compounds of general formula (I), wherein R₁ is an ethyl group, are desired to be obtained, processes (b), (c), (d), (e), and (f) may be stopped, the case being, when the compounds of general formula (IV), wherein X is the carbethoxy group, are obtained.

As hereabove described, esterification of the compounds of general formula (I), wherein R₁ is hydrogen to give, if desired, compounds of general formula (I), wherein R₁ is different from hydrogen, is performed according to the usual methods of organic chemistry, as is known to those skilled in the art. For example, the esters of the compound of general formula (I) wherein R₁ is hydrogen, with N,N-dimethylaminoethanol may be prepared by treatment of said compounds with SOCl₂ at a temperature of about 60° to about 90° C. in the presence or absence of solvents, and subsequently by reacting the acid chlorides, so obtained, with N,N-dimethylaminoethanol at room temperature in apolar solvents, such as, for example, dioxane, benzene, and the like.

The compounds of general formula (I) wherein R₁ is hydrogen, may also be converted, if desired, into their salts with physiologically acceptable inorganic bases, such as, for example, NaOH, Ca(OH)₂, and the like, or organic bases, such as, for example, N,N-dimethylaminoethanol, or the like, according to the usual methods of organic chemistry, as is known to those skilled in the art. For example, the salts of the compounds of general formula (I) wherein R₁ is hydrogen, with N,N-dimethylaminoethanol may be obtained by reacting, at room temperature, these compounds with an aqueous solution containing the stoichiometric quantity of N,N-dimethylaminoethanol and by subsequent lyophilization. The compounds of general formula (I), wherein $R_1$ is the group

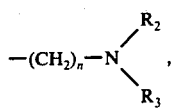

may also be converted, if desired, into their salts with physiologically acceptable organic or inorganic acids, according to the usual methods of organic chemistry, as is known to those skilled in the art.

The compounds, object of the present invention, possess a good analgesic and anti-inflammatory activity, as shown by the data reported in the table 1 herebelow, where phenylbutazone is listed alongside as reference product.

TABLE 1

| Compound | Analgesic activity | Anti-inflammatory activity |
|---|---|---|
| (isoindolinone–phenyl–CH(CH₃)–COOH) | 100 | 20 |
| (isoindolinone–phenyl–CH(C₂H₅)–COOH) | 32 | 8 |
| (isoindolinone–phenyl–CH(CH₃)–COOC₂H₅) | 40 | 13 |
| (isoindolinone–phenyl–CH(CH₃)–COO(CH₂)₂–N(CH₃)₂) | 33 | 11 |
| (isoindolinone–phenyl–CH(CH₃)–COOH · (CH₃)₂N–CH₂CH₂OH) | 54 | 42 |
| Phenylbutazone | 1 | 1 |

Analgesic activity was assessed by means of phenylquinone test in mice according to Siegmund (Siegmund et al., Proc. Soc. Exper. Biol. Med., 95, 729 (1957)).

Anti-inflammatory activity was assessed by means of carrageenin induced edema test in rats according to Winter (Winter et al., Proc. Soc. Exper. Biol. Med., 111, 544 (1962) and J. Pharmac. Exp. Therap., 141, 369 (1963)).

Table 2 shows the anti-inflammatory activity of 1-oxo-2-{p-[(α-methyl)-carboxymethyl]-phenyl}-isoindoline (I) in comparison with α-[3-chloro-4-(1-oxo-2-isoindolinyl)-phenyl]-propionic acid (II), described in Belgian Pat. No. 753,600.

Table 2

| Test | Potency ratio I/II | Limits for P = 0.05 |
|---|---|---|
| Carrageenin induced edema in rat paw | 5.27 | 2.84 – 10.78 |

Table 2-continued

| Test | Potency ratio I/II | Limits for P = 0.05 |
|---|---|---|
| Granuloma pouch test in the rat | 12.66 | 6.60 – 58.58 |

In table 2 anti-inflammatory activity was determined employing both the Winter's method, as previously indicated, and granuloma pouch technique (Boris A., Stevenson R. H., Arch. Int. Pharmacodyn., 153, 205 (1965). The potency ratios were estimated following the parallel line biological assay method (Finney D. I., Statistical Method in Biological Assay — Griffin — London (1952)).

As shown by the data reported in Table 2, it was surprisingly found that the anti-inflammatory activity of 1-oxo-2-{p-[(α-methyl)-carboxymethyl]-phenyl}-isoindoline is much higher than that of α-[3-chloro-4-(1-oxo-2-isoindolinyl)-phenyl]-propionic acid. The pharmacological data hereabove reported have been confirmed by clinical trials performed on man.

The results of such clinical trials have shown that the dosage ranges for adult humans may vary from about 25 to about 150 mg. pro dose, and preferably from about 50 to about 100 mg. pro dose.

The compounds of the present invention are preferably administered orally, but they can also be administered by parentheral or topical way.

The pharmaceutical compositions containing the compounds of this invention can be therefore either capsules, tablets, pills, syrups, or vials, suppositories, ointments.

Examples of the substances which can serve as pharmacological carriers or diluents for the pharmaceutical compositions of the compounds of the invention are talc, gelatin, lactose, starch, magnesium stearate, polyvinylpyrrolidone, as well as other non-toxic compatible substances used in pharmaceutical formulations.

The following examples illustrate, but do not limit, the scope of the present invention.

EXAMPLE 1

A mixture of ethyl p-amino-(α-methyl)-phenylacetate (24.15 g.; 0.125 moles) and o-cyano-benzylbromide (24.5 g.; 0.125 moles) in EtOH 99.9 (400 ml) is heated with a reflux condenser for 6 hours, added with char and filtered during heating. The filtrate is concentrated to about one third and then poured in ethyl ether (1500 ml). The precipitate is filtered and washed again with ethyl ether (100 ml) to obtain 1-imino-2-{p-[(α-methyl)-carbethoxymethyl]-phenyl}-isoindoline. HBr (44.8 g., yield = 92%), m.p. 203°–204° C.

In the same way, and by reacting o-cyano-benzylbromide with the proper amino esters, the following compounds are obtained:

1-imino-2-[p-(carbethoxymethyl)-phenyl]-isoindoline. HBr, m.p. 204°–206° C.

1-imino-2-{p-[(α-ethyl)-carbethoxymethyl]-phenyl}-isoindoline. HBr, m.p. 157°–159° C.

1-imino-2-{p-[(α-propyl)-carbethoxymethyl]-phenyl}-isoindoline. HBr, m.p. 158°–160° C.

1-imino-2-{p-[(α-butyl)-carbethoxymethyl]-phenyl}-isoindoline. HBr, m.p. 140°–142° C.

EXAMPLE 2

1-imino-2-{p-[(α-methyl)-carbethoxymethyl]-phenyl}-isoindoline. HBr, (9.73 g.; 0.025 moles) dissolved in EtOH 95% (65 ml) is added to $K_2CO_3$ (13.82 g.; 0.1 moles) dissolved in water (100 ml). The mixture of the reagents is heated with a reflux condenser under mixing for 18 hours thus obtaining a complete solution. Ethyl alcohol is evaporated under vacuum, the undissolved residue is filtered and the filtrate is acidified with HCl 8% (about 60 ml).

The precipitate thus formed is filtered, washed with water (100 ml), with HCl 8% (30 ml), and again with water (50 ml) to obtain, after crystallization from EtOH 95%, 1-oxo-2-{p-[(α-methyl)-carboxymethyl]-phenyl}-isoindoline (6 g., yield = 85%), m.p. 213°–214° C.

In the same way, and by employing the compounds prepared according to Example 1, the following compounds are obtained:

1-oxo-2-[p-(carboxymethyl)-phenyl]-isoindoline, m.p. 208°–209° C.

1-oxo-2-{p-[(α-ethyl)-carboxymethyl]-phenyl}-isoindoline, m.p. 180°–182° C.

1-oxo-2-{p-[(α-propyl)-carboxymethyl]-phenyl}-isoindoline, m.p. 160°–162° C.

1-oxo-2-{p-[(α-butyl)-carboxymethyl]-phenyl}-isoindoline, m.p. 145°–147° C.

EXAMPLE 3

A mixture of o-cyano-benzylbromide (3.92 g.; 0.02 moles) and p-amino-(α-methyl)-phenylacetic acid (3.3 g.; 0.02 moles) in EtOH 99.9% (80 ml) is heated with a reflux condenser for 6 hours, evaporated to little volume (about 30 ml) under vacuum and then poured in ethyl ether (about 400 ml). The separated solid is crystallized from EtOH ethyl ether to obtain 1-imino-2-{p-[(α-methyl)-carboxymethyl]-phenyl}-isoindoline. HBr (5.77, yield = 80%), m.p. 264°–266° C. (dec.).

This produce dissolved in EtOH 95% (60 ml) is added to $K_2CO_3$ (6.91 g.; 0.05 moles) dissolved in water (50 ml). The mixture of the reagents is refluxed for 12 hours to obtain a complete solution. Ethyl alcohol is evaporated under vacuum, the undissolved residue is filtered and the filtrate is acidified with HCl 8% (about 30 ml). The precipitate thus formed is filtered, washed with water (80 ml), with HCl 8% (15 ml) and again with water (40 ml), to obtain, after crystallization from EtOH 95%, 1-oxo-2-{p-[(α-methyl)-carboxymethyl]-phenyl}-isoindoline (4.7 g., yield = 84%), m.p. 213°–214° C.

In the same way, and by reacting o-cyano-benzylbromide with the proper amino acids, the following compounds are obtained:

1-oxo-2-[p-(carboxymethyl)-phenyl]-isoindoline, m.p. 208°–209° C.

1-oxo-2-{p-[(α-ethyl)-carboxymethyl]-phenyl}-isoindoline, m.p. 180°–182° C.

1-oxo-2-{p-[(α-propyl)-carboxymethyl]-phenyl}-isoindoline, m.p. 160°–162° C.

1-oxo-2-{p-[(α-butyl)-carboxymethyl]-phenyl}-isoindoline, m.p. 145°–147° C.

EXAMPLE 4

Phthalide (2.7 g.; 0.02 moles) and ethyl p-amino (α-methyl)-phenylacetate (11.6 g.; 0.06 moles) are heated to 280° for 4 hours in a sealed tube, then cooled, treated with water (100 ml), acidified with HCl 8% (40 ml), and extracted with ethyl acetate (200 ml). The organic layer is washed with water (80 ml), dried and evaporated to dryness in vacuum. The oily residue is crystallized from ligroin to obtain 1-oxo-2-{p-[(α-methyl)-carbethoxymethyl]-phenyl}-isoindoline (4.32 g., yield = 70%), m.p. 99°–101° C.

In the same way, and by reacting phthalide with the proper amino esters, the following compounds are obtained:

1-oxo-2-[p-(carbethoxymethyl)-phenyl]-isoindoline, m.p. 122°–124° C.

1-oxo-2-{p-[(α-ethyl)-carbethoxymethyl]-phenyl}-isoindoline, m.p. 107°–109° C.

1-oxo-2-{p-[(α-propyl)-carbethoxymethyl]-phenyl}-isoindoline, m.p. 105°–106° C.

1-oxo-2-{p-[(α-butyl)-carbethoxymethyl]-phenyl}-isoindoline, m.p. 106°–107° C.

EXAMPLE 5

Tiophthalide (1.5 g.; 0.01 moles) and ethyl p-amino-(α-methyl)-phenylacetate (5.8 g.; 0.03 moles) are heated to 190°–200° for 3 hours in a sealed tube, then cooled, treated with water (50 ml), acidified with HCl 8% (20 ml), and extracted with ethyl acetate (50 ml). The organic layer is washed with water (40 ml), dried and evaporated to dryness in vacuum. The residue is crystallized from ligroin to obtain 1-oxo-2-{p-[(α-methyl)-carbethoxymethyl]-phenyl}isoindoline (2.32 g., yield = 75%), m.p. 99°–101° C.

In the same way, and by reacting tiophthalide with the proper amino esters, the following compounds are obtained:

1-oxo-2-[p-(carbethoxymethyl)-phenyl]-isoindoline, m.p. 122°–124° C.

1-oxo-2-{p-[(α-ethyl)-carbethoxymethyl]-phenyl}-isoindoline, m.p. 107°–109° C.

1-oxo-2-{p-[(α-propyl)-carbethoxymethyl]-phenyl}-isoindoline, m.p. 105°–106° C.

1-oxo-2-{p-[(α-butyl)-carbethoxymethyl]-phenyl}-isoindoline, m.p. 106°–107° C.

EXAMPLE 6

To a solution of phthalic aldehyde (2.94 g.; 0.022 moles) suspended in dimethylformamide (200 ml), heated to 60°, ethyl p-amino-(α-methyl)-phenylacetate (3.86 g.; 0.02 moles), dissolved in dimethylformamide (150 ml), is added in the course of an hour. The mixture is stirred again for 2 hours at 60°, the solvent is evaporated under vacuum. The oily residue is dissolved in ethyl acetate (80 ml), washed with HCl 8% (15 ml) and with water (30 ml). The organic layer is dried, evaporated to dryness under vacuum, and the residue is cristallized from ligroin to obtain 1-oxo-2-{p-[(α-methyl)-carbethoxymethyl]-phenyl}-isoindoline (5.25 g., yield = 85%), m.p. 99°–101° C.

In the same way, and by reacting phthalic aldehyde with the proper amino esters, the following compounds are obtained:

1-oxo-2-[p-(carbethoxymethyl)-phenyl]-isoindoline, m.p. 122°–124° C.

1-oxo-2-{p-[(α-ethyl)-carbethoxymethyl]-phenyl}-isoindoline, m.p. 107°–109° C.

1-oxo-2-{p-[(α-propyl)-carbethoxymethyl]-phenyl}-isoindoline, m.p. 105°–106° C.

1-oxo-2-{p-[(α-butyl)-carbethoxymethyl]-phenyl}-isoindoline, m.p. 106°–107° C.

EXAMPLE 7

A mixture of phthalic anhydride (14.8 g.; 0.1 moles) and ethyl p-amino-(α-methyl)-phenylacetate (19.3 g.; 0.1 moles) in glacial acetic acid (70 ml) is heated with a reflux condenser for 4 hours, then cooled at about 40°, and diluted with water (50 ml). An oily precipitate, thus formed, solidifies after rubbing, is then cooled at 0°, filtered and washed with water (40 ml), to obtain, after crystallization from EtOH 99,9%, N-{4-[(α-methyl)-carbethoxymethyl]-phenyl}-phthalimide (30 g., yield = 93%), m.p. 113°–114° C.

In the same way, and by reacting phthalic anhydride with the proper amino esters, the following compounds are obtained:

N-[4-(carbethoxymethyl)-phenyl]-phthalimide, m.p. 150°–152° C.

N-{4-[(α-ethyl)-carbethoxymethyl]-phenyl}-phthalimide, m.p. 108°–109° C.

N-{4-[(α-propyl)-carbethoxymethyl]-phenyl}-phthalimide, m.p. 119°–121° C.

N-{4-[(α-butyl)-carbethoxymethyl]-phenyl}-phthalimide, m.p. 80°–82° C.

EXAMPLE 8

A mixture of phthalic acid (16.6 g.; 0.1 moles) and ethyl p-amino-(α-methyl)-phenyl-acetate (20 g.; 0.103 moles) is heated in an oil bath at 200°–210° for an hour and a quarter, then cooled, to obtain, after crystallization from EtOH 99%, N-{4-[(α-methyl)-carbethoxymethyl]-phenyl}-phthalimide (31 g., yield = 96%), m.p. 113°–114° C.

In the same way, and by reacting phthalic acid with the proper amino esters, the following compounds are obtained:

N-[4-(carbethoxymethyl)-phenyl]-phthalimide, m.p. 150°–152° C.

N-{4-[(α-ethyl)-carbethoxymethyl]-phenyl}-phthalimide, m.p. 108°–109° C.

N-{4-[(α-propyl)-carbethoxymethyl]-phenyl}-phthalimide, m.p. 119°–121° C.

N-{4-[(α-butyl)-carbethoxymethyl]-phenyl}-phthalimide, m.p. 80°–82° C.

EXAMPLE 9

Ethyl ester of phthalic acid (4.44 g.; 0.02 moles) and ethyl p-amino-(α-methyl)-phenyl-acetate (3.86 g.; 0.02 moles) suspended in anhydrous dimethylformamide (100 ml) are heated with a reflux condenser for 4 hours. The mixture is evaporated to dryness under vacuum, the residue is redissolved in ethyl acetate (100 ml), then washed with HCl 8% (15 ml), with water (40 ml), dried and evaporated to dryness under vacuum, to obtain, after crystallization from EtOH 99%, N-{4-[(α-methyl)-carbethoxymethyl]-phenyl}-phthalimide (4.52 g.; yield = 70%), m.p. 113°–114° C.

In the same way, and by reacting ethyl ester of phthalic acid with the proper amino esters, the following compounds are obtained:

N-[4-(carbethoxymethyl)-phenyl]-phthalimide, m.p. 150°–152° C.

N-{4-[(α-ethyl)-carbethoxymethyl]-phenyl}-phthalimide, m.p. 108°–109° C.

N-{4-[(α-propyl)-carbethoxymethyl]-phenyl}-phthalimide, m.p. 119°–121° C.

N-{4-[(α-butyl)-carbethoxymethyl]-phenyl}-phthalimide, m.p. 80°–82° C.

EXAMPLE 10

To a solution of N-{4-[(α-methyl)-carbethoxymethyl]-phenyl}-phthalimide (16.1 g.; 0.05 moles) suspended in acetic acid (200 ml), Zn in powder (19.6 g.; 0.3 moles) is added under stirring. The mixture is heated with a reflux condenser for 4 hours, filtered, and the residue is then washed with warm acetic acid (40 ml). The filtrate is evaporated to dryness under vacuum, the residue is redissolved in water (100 ml) and neutralized with sodium bicarbonate to give pH = 7. The solid, thus formed, is filtered to obtain, after crystallization from ligroin, 1-oxo-2-{p-[(α-methyl)-carbethoxymethyl]-phenyl}-isoindoline (13.9 g., yield = 90%), m.p. 99°–101° C.

In the same way, and starting from phthalimides prepared according to Examples 7, 8 and 9, the following compounds are obtained:

1-oxo-2-[p-(carbethoxymethyl)-phenyl]-isoindoline, m.p. 122°–124° C.

1-oxo-2-{p-[(α-ethyl)-carbethoxymethyl]-phenyl}-isoindoline, m.p. 107°–109° C.

1-oxo-2-{p-[(α-propyl)-carbethoxymethyl]-phenyl}-isoindoline, m.p. 105°–106° C.

1-oxo-2-{p-[(α-butyl)-carbethoxymethyl]-phenyl}-isoindoline, m.p. 106°–107° C.

EXAMPLE 11

A mixture of 1-oxo-2-{p-[(α-methyl)-carbethoxymethyl]-phenyl}-isoindoline (12.36 g.; 0.04 moles) and K$_2$CO$_3$ (12.36 g.) in EtOH 95% (280 ml) and water (182 ml) is heated with a reflux condenser for 8 hours to obtain a complete solution. Ethyl ether is evaporated under vacuum, the aqueous solution is acidified with HCl 8% (55 ml), and the precipitate, thus formed, is filtered, washed with water (55 ml), to obtain, after crystallization from EtOH 95%, 1-oxo-2-{p-[(α-methyl)-carboxymethyl]-phenyl}-isoindoline (9.1 g., yield = 81%), m.p. 213°–214° C.

In the same way, and starting from the derivatives prepared according to Examples 4, 5, and 6, the following compounds are obtained:

1-oxo-2-[p-(carboxymethyl)-phenyl]-isoindoline, m.p. 208°–209° C.
1-oxo-2-{p-[(α-ethyl)-carboxymethyl]-phenyl}-isoindoline, m.p. 180°–182° C.
1-oxo-2-{p-[(α-propyl)-carboxymethyl]-phenyl}-isoindoline, m.p. 160°–162° C.
1-oxo-2-{p-[(α-butyl)-carboxymethyl]-phenyl}-isoindoline, m.p. 145°–147° C.

EXAMPLE 12

A mixture of o-cyano-benzylbromide (3.92 g.; 0.02 moles) and p-amino-(α-methyl)-phenyl-acetonitrile (2.92 g.; 0.02 moles) in EtOH 99,9% (80 ml) is heated with a reflux condenser for 6 hours and evaporated under vacuum (about 15 ml). The precipitate, thus formed, is filtered to obtain 1-imino-2-{p-[(α-methyl)-carbonitrile-methyl]-phenyl}-isoindoline. HBr (5.47 g., yield = 80%), m.p. 253°–255° C.

In the same way, and by reacting o-cyano-benzylbromide with the proper aminonitriles, the following compounds are obtained:
1-imino-2-[p-(carbonitrile-methyl)-phenyl]-isoindoline. HBr
1-imino-2-{p-[(α-ethyl)-carbonitrile-methyl]-phenyl}-isoindoline. HBr
2-imino-2-{p-[(α-propyl)-carbonitrile-methyl]-phenyl}-isoindoline. HBr
1-imino-2-{p-[(α-butyl)-carbonitrile-methyl]-phenyl}-isoindoline. HBr

EXAMPLE 13

To 1-imino-2-{p-[(α-methyl)-carbonitrile-methyl]-phenyl}-isoindoline. HBr (3.42 g.; 0.01 moles) dissolved in EtOH 99,9% (80 ml), $K_2CO_3$ (5.52 g.) dissolved in water (20 ml) is added. The mixture is heated with a reflux condenser for 10 hours and filtered. The residue is washed with water (50 ml) to obtain, after crystallization from EtOH 99.9%, 1-oxo-2-{p-[(α-methyl)-carbonitrile-methyl]-phenyl}-isoindoline (2.22 g., yield = 85%), m.p. 192°–194° C.

In the same way, and starting from the derivatives prepared according to Example 12, the following compounds are obtained:
1-oxo-2-[p-(carbonitrile-methyl)-phenyl]-isoindoline.
1-oxo-2-{p-[(α-ethyl)-carbonitrile-methyl]-phenyl}-isoindoline.
1-oxo-2-{p-[(α-propyl)-carbonitrile-methyl]-phenyl}-isoindoline.
1-oxo-2-{p-[(α-butyl)-carbonitrile-methyl]-phenyl}-isoindoline.

EXAMPLE 14

A mixture of phthalide (2.7 g.; 0.02 moles) and p-amino-(α-methyl)-phenyl-acetonitrile (8.8 g.; 0.06 moles) is heated to 280° for 4 hours in a sealed tube, cooled, treated with water (100 ml), acidified with HCl 8% (40 ml) and extracted with ethyl acetate (200 ml). The organic layer is washed with water (80 ml), dried and evaporated to dryness under vacuum. The residue is crystallized from EtOH 99.9% to obtain 1-oxo-2-{p-[(α-methyl)-carbonitrile-methyl]-phenyl}-isoindoline (3.57 g., yield = 68%), m.p. 192°–194° C.

In the same way, and by reacting phthalide with the proper amino nitriles, the following compounds are obtained:
1-oxo-2-[p-(carbonitrile-methyl)-phenyl]-isoindoline
1-oxo-2-{p-[(α-ethyl)-carbonitrile-methyl]-phenyl}-isoindoline
1-oxo-2-{p-[(α-propyl)-carbonitrile-methyl]-phenyl}-isoindoline
1-oxo-2-{p-[(α-butyl)-carbonitrile-methyl]-phenyl}-isoindoline

EXAMPLE 15

A mixture of tiophthalide (3 g.; 0.02 moles) and p-amino-(α-methyl)-phenyl-acetonitrile (8.8 g.; 0.06 moles) is heated to 210°–220° C. for 4 hours in a sealed tube, cooled, redissolved in water (100 ml), acidified with HCl 8% (40 ml), and extracted with ethyl acetate (150 ml). The organic layer is washed with water (80 ml), dried and evaporated to dryness under vacuum. The residue is crystallized from EtOH 99.9% to obtain 1-oxo-2-{p-[(α-methyl)-carbonitrile-methyl]-phenyl}-isoindoline (3.67 g., yield = 70%), m.p. 192°–194° C.

In the same way, and by reacting tiophthalide with the proper amino nitriles, the following compounds are obtained:
1-oxo-2-[p-(carbonitrile-methyl)-phenyl]-isoindoline
1-oxo-2-{p-[(α-ethyl)-carbonitrile-methyl]-phenyl}-isoindoline
1-oxo-2-{p-[(α-propyl)-carbonitrile-methyl]-phenyl}-isoindoline
1-oxo-2-{p-[(α-butyl)-carbonitrile-methyl]-phenyl}-isoindoline

EXAMPLE 16

To a solution of phthalic aldehyde (2.94 g.; 0.022 moles) suspended in dimethylformamide (200 ml), heated to 60° C., p-amino-(α-methyl)-phenyl-acetonitrile (2.92 g.; 0.02 moles), dissolved in dimethylformamide (100 ml), is added in the course of an hour. The mixture is stirred again for 4 hours at 60° C., the solvent is evaporated under vacuum. The oily residue is dissolved in ethyl acetate (100 ml), washed with HCl 8% (15 ml), then with water (30 ml). The organic layer is dried and evaporated to dryness under vacuum. The residue is crystallized from EtOH 99.9% to obtain 1-oxo-2-{p-[(α-methyl)-carbonitrile-methyl]-phenyl}-isoindoline (3.94 g., yield = 75%), m.p. 192°–194° C.

In the same way, and by reacting phthalic aldehyde with the proper amino nitriles, the following compounds are obtained:
1-oxo-2-[p-(carbonitrile-methyl)-phenyl]-isoindoline
1-oxo-2-{p-[(α-ethyl)-carbonitrile-methyl]-phenyl}-isoindoline
1-oxo-2-{p-[(α-propyl)-carbonitrile-methyl]-phenyl}-isoindoline
1-oxo-2-{p-[(α-butyl)-carbonitrile-methyl]-phenyl}-isoindoline

EXAMPLE 17 a mixture of phthalic anhydride (17.8 g.; 0.12 moles) and p-amino-(α-methyl)-phenyl-acetonitrile (14.61 g.; 0.1 moles) in glacial acetic acid (90 ml) is heated with a reflux condenser for 4 hours thus obtaining a complete solution. The mixture is then cooled, and the solid separated is filtered, washed with water and dried to obtain N-{4-[(α-methyl)-carbonitrile-methyl]-phenyl}-phthalimide (22.1 g., yield = 80%), m.p. 213°–215° C.

In the same way, and by reacting phthalic anhydride with the proper amino nitriles, the following compounds are obtained:
N-[4-(carbonitrile-methyl)-phenyl]-phthalimide
N-{4-[(α-ethyl)-carbonitrile-methyl]-phenyl}-phthalimide N-{4-[(α-propyl)-carbonitrile-methyl]-phenyl}-phthalimide N-{4-[(α-butyl)-carbonitrile-methyl]-phenyl}-phthalimide

EXAMPLE 18

A mixture of phthalic acid (3.32 g.; 0.02 moles) and p-amino-(α-methyl)-phenyl-acetonitrile (2.96 g.; 0.02 moles) is heated in an oil bath to 220°-230° C. for an hour and a half, then cooled, redissolved with water and the solid, thus formed, is filtered to obtain N-{4-[(α-methyl)-carbonitrile-methyl]-phenyl}-phthalimide (4.68 g.; yield = 85%), m.p. 213°-215° C.

In the same way, and by reacting phthalic acid with the proper amino nitriles, the following compounds are obtained:
N-[4-(carbonitrile-methyl)-phenyl]-phthalimide
N-{4-[(α-ethyl)-carbonitrile-methyl]-phenyl}-phthalimide
N-{4-[(α-propyl)-carbonitrile-methyl]-phenyl}-phthalimide
N-{4-[(αbutyl)-carbonitrile-methyl]-phenyl}-phthalimide

EXAMPLE 19

A mixture of ethyl ester of phthalic acid (4.44 g.; 0.02 moles) and p-amino-(α-methyl)-phenyl-acetonitrile (2.96 g.; 0.02 moles) suspended in anhydrous dimethylformamide (100 ml) is heated with a reflux condenser for 4 hours, evaporated to dryness under vacuum, the residue is then redissolved with ethyl acetate (100 ml), washed with HCl 8% (15 ml), then with water (40 ml), subsequently dried and evaporated to dryness under vacuum. The residue is crystallized from EtOH 99% to obtain N-{4-[(α-methyl)-carbonitrile-methyl]-phenyl}-phthalimide (4.13 g., yield = 75%), m.p. 213°-215° C.

In the same way, and by reacting ethyl ester of phthalic acid with the proper amino nitriles, the following compounds are obtained:
N-[4-(carbonittrile-methyl)-phenyl]-phthalimide
N-{4-[(α-ethyl)-carbonitrile-methyl]-phenyl}-phthalimide
N-{4-[(α-propyl)-carbonitrile-methyl]-phenyl}-phthalimide
N-{4-[(α-butyl)-carbonitrile-methyl]-phenyl}-phthalimide

EXAMPLE 20

To a suspension of N-{4-[(α-methyl)-carbonitrile-methyl]-phenyl}-phthalimide (2.76 g.; 0.01 moles) in glacial acetic acid (50 ml), heated to 70° C., Zn in powder (4 g.) is added gradually. The mixture is then heated with a reflux condenser for 14 hours. The inorganic layer is filtered, the filtrate is cooled, and the solid product, thus formed, is filtered, treated with water, then with NaHCO₃ 8% (50 ml), and filtered again. The residue is crystallized from EtOH 99.9% to obtain 1-oxo-2-{p-[(α-methyl)-carbonitrile-methyl]-phenyl}-isoindoline (1.83 g., yield = 70%), m.p. 192°-194° C.

In the same way, and starting from the derivative prepared according to Example 17, 18 and 19, the following compounds are obtained:
1-oxo-2-[p-(carbonitrile-methyl)-phenyl]-isoindoline
1-oxo-2-{p-[(α-ethyl)-carbonitrile-methyl]-phenyl}-isoindoline
1-oxo-2-{p-[(α-propyl)-carbonitrile-methyl]-phenyl}-isoindoline
1-oxo-2-{p-[(α-butyl)-carbonitrile-methyl]-phenyl}-isoindoline

EXAMPLE 21

A suspension of 1-oxo-2-{p-[(α-methyl-carbonitrile-methyl]-phenyl}-isoindoline (2.62 g.; 0.01 moles) in conc. H₂SO₄ (2.42 ml) and water (7.4 ml) is heated with a reflux condenser for 16 hours, then poured into cold water (100 ml). The solid separated is filtered, then treated with NaOH 8% (30 ml). The insoluble residue is filtered, the filtrate is acidified with HCl 8% (30 ml), the solid is filtered and crystallized from EtOH 95% to obtain 1-oxo-2-{p-[(α-methyl)-carboxymethyl]-phenyl}-isoindoline (2.39 g., yield = 85%), m.p. 213°-214° C.

In the same way, and starting from the derivative prepared according to Example 14, 15 and 20, the following compounds are obtained:
1-oxo-2[p-(carboxymethyl)-phenyl]-isoindoline, m.p. 208°-209° C.
1-oxo-2-{p-[(α-ethyl)-carboxymethyl]-phenyl}-isoindoline, m.p. 180°-182° C.
1-oxo-2-{p-[(α-propyl)-carboxymethyl]-phenyl}-isoindoline, m.p. 160°-162° C.
1-oxo-2-{p-[(α-butyl)-carboxymethyl]-phenyl}-isoindoline, m.p. 145°-147° C.

EXAMPLE 22

A solution of 1-oxo-2-{p-[(α-methyl)-carboxymethyl]-phenyl}-isoindoline (15.4 g.; 0.055 moles) and concentrated sulfuric acid (6 ml) in anhydrous methyl alcohol (180 ml) is heated with a reflux condenser for 6 hours, then cooled and filtered, and the precipitate is washed with NaHCO₃ 2% (100 ml) to obtain, after crystallization from methyl alcohol, 1-oxo-2-{p-[(α-methyl)-carbomethoxy-methyl]-phenyl}-isoindoline (15.5 g., yield = 96%), m.p. 124°-126° C.

In the same way, and by reacting methyl alcohol with the proper isoindolines, the following compounds are obtained:
1-oxo-2-[p-(carbomethoxy-methyl)-phenyl]-isoindoline
1-oxo-2-{p-[(α-ethyl)-carbomethoxy-methyl]-phenyl}-isoindoline
1-oxo-2-{p-[(α-propyl)-carbomethoxy-methyl]-phenyl}-isoindoline
1-oxo-2-{p-[(α-butyl)-carbomethoxy-methyl]-phenyl}-isoindoline

EXAMPLE 23

A solution of 1-oxo-2-{p-[(α-methyl)-carboxymethyl]-phenyl}-isoindoline (20 g.; 0.0714 moles) and SOCl₂ (120 ml) is heated with a reflux condenser for 3 hours, the excess SOCl₂ is then distilled away, then anhydrous benzene (150 ml) is added, and after evaporation to dryness, treatment with petroleum ether, a solid is filtered, which by crystallization from a mixture of benzene and petroleum ether gives the acid chloride of 1-oxo-2-{p-[(α-methyl)-carboxymethyl]-phenyl}-isoindoline (18.15 g., yield = 85%), m.p. 132°-134° C.

This acid chloride (12 g.) is now dissolved in anhydrous dioxane (200 ml), and this solution is added dropwise, under effective agitation, to a solution of N,N-dimethylaminoethanol (12 ml) in anhydrous dioxane (200 ml) to produce a slightly exothermic reaction. The mixture is agitated for 3 hours at room temperature, then let stand overnight. The precipitate thus formed is then filtered, and the filtrate is evaporated under vacuum to make an oily residue. This residue is dissolved in CHCl₃ (150 ml), the chloroform solution is washed with NaHCO₃ 2% (100 ml), dried on anhydrous sodium sulfate and evaporated to dryness under vacuum. The residue is then extracted with hot hexane, and subsequently cooled to obtain N,N-dimethylaminoethanol ester of 1-oxo-2-{p-[(α-methyl)-carboxymethyl]-phenyl}-isoindoline (11.3 g., yield = 80%), m.p. 61°-63° C.

In the same way, and by reacting N,N-dimethylaminoethanol with the acid chlorides of the proper isoindolines, the following compounds are obtained:

N,N-dimethylaminoethanol ester of 1-oxo-2-[p-(carboxymethyl)-phenyl]-isoindoline
N,N-dimethylaminoethanol ester of 1-oxo-2-{p-[(α-ethyl)-carboxymethyl]-phenyl}-isoindoline
N,N-dimethylaminoethanol ester of 1-oxo-2-{p-[(α-propyl)-carboxymethyl]-phenyl}-isoindoline
N,N-dimethylaminoethanol ester of 1-oxo-2-{p-[(α-butyl)-carboxymethyl]-phenyl}-isoindoline.

EXAMPLE 24

N,N-dimethylaminoethanol (1 ml) is added to 1-oxo-2-{p-[(α-methyl)-carboxymethyl]-phenyl}-isoindoline (2.8 g.; 0.01 moles), suspended in water (100 ml). The solution is then lyophilized to obtain N,N-dimethylaminoethanol salt of 1-oxo-2-{p-[(α-methyl)-carboxymethyl]-phenyl}-isoindoline (3.7 g., yield = 100%).

In the same way, and by reacting N,N-dimethylaminoethanol with the proper isoindolines, the following compounds are obtained:

N,N-dimethylaminoethanol salt of 1-oxo-2-[p-(carboxymethyl)-phenyl]-isoindoline
N,N-dimethylaminoethanol salt of 1-oxo-2-{p-[(α-ethyl)-carboxymethyl]-phenyl}-isoindoline
N,N-dimethylaminoethanol salt of 1-oxo-2-{p-[(α-propyl)-carboxymethyl]-phenyl}-isoindoline
N,N-dimethylaminoethanol salt of 1oxo-2-{p-[(α-butyl)-carboxymethyl]-phenyl}-isoindoline.

We claim:
1. The treatment of pains, said treatment comprising administering to a patient in need of such treatment a therapeutically effective amount of a compound of the formula:

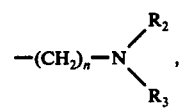

wherein R is a member selected from the group consisting of hydrogen and lower alkyl of 1 to 4 carbon atoms, and R₁ is a member selected from the group consisting of hydrogen, lower alkyl of 1 to 4 carbon atoms and a group of general formula

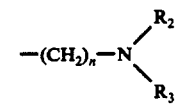

wherein $n$ is 1 or 2 and $R_2$ and $R_3$ are independently selected from the group consisting of hydrogen and lower alkyl of 1 to 4 carbon atoms; a salt of a compound of general formula (I), wherein $R_1$ is hydrogen, with a physiologically acceptable base or a salt of a compound of general formula (I), wherein $R_1$ is the group $$-(CH_2)_n-N\begin{matrix}R_2\\R_3\end{matrix}$$

with a physiologically acceptable acid.

2. The treatment as claimed in claim 1, wherein said therapeutically effective amount is from about 25 mg pro dose to about 100 mg pro dose for adult humans.

* * * * *

Notice of Adverse Decision in Interference

In Interference No. 100,553, involving Patent No. 4,118,504, P. N. Giraldi, G. Nannini, W. Logemann, R. Tommasini, A. Buttinoni and G. Biasoli, ISOINDOLINE DERIVATIVES FOR TREATING PAIN, final judgment adverse to the patentees was rendered Sept. 24, 1981, as to claims 1 and 2.
[*Official Gazette March 7, 1989.*]